US007431931B2

(12) United States Patent
Kapikian et al.

(10) Patent No.: US 7,431,931 B2
(45) Date of Patent: Oct. 7, 2008

(54) COMPOSITIONS AND METHOD FOR PREVENTING REACTOGENICITY ASSOCIATED WITH ADMINISTRATION OF IMMUNOGENIC LIVE ROTAVIRUS COMPOSITIONS

(75) Inventors: Albert Z. Kapikian, Rockville, MD (US); Robert Chanock, Bethesda, MD (US); Timo Vesikari, Tampere (FI)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 363 days.

(21) Appl. No.: 10/181,908

(22) PCT Filed: Jan. 26, 2001

(86) PCT No.: PCT/US01/02686

§ 371 (c)(1),
(2), (4) Date: Aug. 8, 2003

(87) PCT Pub. No.: WO01/54718

PCT Pub. Date: Aug. 2, 2001

(65) Prior Publication Data
US 2004/0223981 A1 Nov. 11, 2004

Related U.S. Application Data

(60) Provisional application No. 60/178,689, filed on Jan. 28, 2000.

(51) Int. Cl.
A61K 39/15 (2006.01)
A61K 39/12 (2006.01)
(52) U.S. Cl. ............... 424/215.1; 424/204.1; 424/205.1
(58) Field of Classification Search ............... 424/215.1, 424/204.1, 205.1
See application file for complete search history.

(56) References Cited

U.S. PATENT DOCUMENTS 4,571,385 A 2/1986 Greenberg et al.

OTHER PUBLICATIONS

Midthun and Kapikian, Rotavirus Vaccines: an Overview, Clinical Microbiology Reviews, Jul. 1996, vol. 9, No. 3 pp. 423-434.*
Clements-Mann et al., Safety and Immunogenicity of live attenuated human-bovine reassortant rotavirus vaccines with VP7-specificity for serotypes 1, 2, 3 or 4 in adults, children and infants, Vaccine, 1999, vol. 17, Issues 20-21, pp. 2715-2725.*
Bernstein et al., "Evaluation of WC3 rotavirus vaccine and correlates of protection in healthy infants," *J. Infect. Dis.* 162:1055-1062 (1990).

Bernstein et al., "Evaluation of rhesus rotavirus monovalent and tetravalent reassortant vaccines in US children. US Rotavirus Vaccine Efficacy Group," *JAMA* 273:1191-1196 (1995).
Christy et al., "Evaluation of a bovine-human rotavirus reassortant vaccine in infants," *J. Infect. Dis.* 168:1598-1599 (1993).
Clark et al., "Immune response of infants and children to low-passage bovine rotavirus (strain WC3)," *Am. J. Dis. Child.* 140:350-356 (1986).
Clark et al., "Immune protection of infants against rotavirus gastroenteritis by a serotype 1 reassortant of bovine rotavirus WC3," *J. Infect. Dis.* 161:1099-1104 (1990).
Clark et al., "Serotype 1 reassortant of bovine rotavirus WC3, strain WI79-9, induces a polytypic antibody response in infants," *Vaccine* 8:327-332 (1990).
Clements-Mann et al., "Safety and immunogenicity of live attenuated human-bovine (UK) reassortant rotavirus vaccines with VP7-specificity for serotypes 1, 2, 3 or 4 in adults, children and infants," *Vaccine* 17:20-21 (1999).
Dagan et al., "Safety and immunogenicity of oral tetravalent human-rhesus reassortant vaccine in neonates," *Pediatr. Infect. Dis. J* 11:991-996 (1992).
Flores et al., "Reactions to and antigenicity of two human-rhesus rotavirus reassortant vaccine candidates of serotypes 1 and 2 in Venezuelan infants," *J. Clin. Microbiol.* 27:512-518 (1989).
Flores et al., "Comparison of reactogenicity and antigenicity of M37 rotavirus vaccine and rhesus-rotavirus-based quadrivalent vaccine," *Lancet* 336:330-3374 (1990).
Flores et al., "Reactogenicity and immunogenicity of a high-titer rhesus rotavirus-based quadrivalent rotavirus vaccine," *J. Clin. Microbiol.* 31:2439-2445 (1993).
Gay et al., "Rotavirus vaccination and intussusception," *Lancet* 354:956 (1999).
Green et al., "Comparison of the amino acid sequences of the major neutralization protein of four human rotavirus serotypes," *Virology* 161:153-159 (1987).
Green et al., "Prediction of human rotavirus serotype by nucleotide sequence analysis of the VP7 protein gene," *J. Virol.* 62:1819-1823 (1988).

(Continued)

Primary Examiner—Bruce Campell
Assistant Examiner—Sharon Hurt
(74) Attorney, Agent, or Firm—Townsend and Townsend and Crew, LLP

(57) ABSTRACT

The present invention provides compositions for making a medicament and methods for the administration of a vaccine compositions for protection against human rotaviral disease without significant reactogenicity. Human x rhesus reassortant rotavirus compositions were made which when administered during the first 7 to about 10 days of life, provided a composition which was non-reactogenic followed by booster immunizations at 16 to 18 weeks or 14 to 20 weeks, up to 1 year of age. The immune response induced by the initial neonatal administration of the live rotavirus vaccine composition protects the infant from the reactogenicity of the composition when administered as a second vaccine dose at or after 2 months of age. Administration of the immunogenic composition also is expected to ablate or significantly diminish the increase in the excess of intussusception observed 3 to 7 days following administration of the initial dose of rotavirus vaccine at about 2 to 4 months.

14 Claims, No Drawings

OTHER PUBLICATIONS

Green et al., "Sequence analysis of the gene encoding the serotype-specific glycoprotein (VP7) of two new human rotavirus serotypes," *Virology* 168:429-433 (1989).

Green et al., "Homotypic and heterotypic epitope-specific antibody responses in adult and infant rotavirus vaccinees: implications for vaccine development," *J. Infect. Dis.* 161:667-679 (1990).

Halsey et al., "Human-rhesus reassortant rotavirus vaccines: safety and immunogenicity in adults, infants, and children," *J. Infect Dis.* 158:1261-1267 (1988).

Hoshino et al., "Serotypic characterization of rotaviruses derived from asymptomatic human neonatal infections," *J. Clin. Microbiol.* 21:425-430 (1985).

Joensuu et al., "Randomised placebo-controlled trial of rhesus-human reassortant rotavirus vaccine for prevention of severe rotavirus gastroenteritis," *Lancet* 350:1205-1209 (1997).

Kapikian et al., "Rhesus rhotavirus: A candidate vaccine for prevention of human rotavirus disease," *Vaccines* 85, Chanock et al., eds., Cold Spring Harbor Laboratory Press, Cold Spring Harbor, New York, pp. 357-367 (1985).

Kapikian et al., "Development of a rotavirus vaccine by a 'Jennerian' and a modified 'Jennerian' approach," *Vaccines* 88, Chanock et al., eds., Cold Spring Harbor Laboratory Press, Cold Spring Harbor, New York, pp. 151-159 (1988).

Kapikian et al., "An update on the 'Jennerian' and modified 'Jennerian' approach to vaccination of infants and young children against rotavirus diarrhea," *Adv. Exp. Med. Biol.* 327:59-69 (1992).

Kapikian et al., "Jennerian and modified Jennerian approach to vaccination against rotavirus diarrhea using a quadrivalent rhesus rotavirus (RRV) and human-RRV reassortant vaccine," *Arch. Virol.* 12:163-175 (1996).

Kapikian et al., "Efficacy of a quadrivalent rhesus rotavirus-based human rotavirus vaccine aimed at preventing severe rotavirus diarrhea in infants and young children," *J. Infect. Diseases* 174:S65-72 (1996).

Madore et al., "Field trial of rhesus rotavirus or human-rhesus rotavirus reassortant vaccine of VP7 serotype 3 or 1 specificity in infants," *J. Infect. Dis.* 166:235-243 (1992).

Midthun and Kapikian, "Rotavirus Vaccines: An Overview," *Clinical Microbiology Reviews*, US, Wa, DC, 9(3):432-434 (1996).

Midthun et al., "Reassortant rotaviruses as potential live rotavirus vaccine candidates," *J. Virol.* 53:949-954 (1985).

Midthun et al., "Single gene substitution rotavirus reassortants containing the major neutralization protein (VP7) of human rotavirus serotype 4," *J. Clin. Microbiol.* 24:822-826 (1986).

Midthun et al., "Comparison of immunoglobulin A (IgA), IgG, and IgM enzyme-linked immunosorbent assays, plaque reduction neutralization assay, and complement fixation in detecting seroresponses to rotavirus vaccine candidates," *J. Clin. Microbiol.* 27:2799-2804 (1989).

Nakagomi et al., "Isolation and molecular characterization of a serotype 9 human rotavirus strain," *Microbiol. Immunol.* 34:77-82 (1990).

Perez-Schael et al., "Clinical studies of a quadrivalent rotavirus vaccine in Venezuelan infants," *J. Clin. Microbiol.* 28:553-558 (1990).

Ramin Shadman, "The withdrawl of the rotashield rotavirus vaccination due to an association with intussusception: fact or fiction?", *Vaccine Revolution Papers, Stanford University*, pp. 1-5 (2000).

Rennels et al., "Lack of an apparent association between intussusception and wild or vaccine rotavirus infection," *Ped Infant* 10:924-925 (1998).

Simasathien et al., "Vaccination of Thai infants with rhesus-human reassortant tetravalent oral rotavirus vaccine," *Pediatr. Infect. Dis. J.* 13:590-596 (1994).

Taniguichi et al., "Antibody response to serotype-specific and cross-reactive neutralization epitopes on VP4 and VP7 after rotavirus infection or vaccination," *J. Clin. Microbiol.* 29:483-487 (1991).

Timenetsky et al., "A novel human rotavirus serotype with dual G5-G11 specificity," *J. Gen. Virol.* 78:1373-1378 (1997).

Treanor et al., "Evaluation of the protective efficacy of a serotype 1 bovine-human rotavirus reassortant vaccine in infants," *Pediatr. Infect. Dis. J.* 14:301-307 (1995).

Vesikari et al., "Immunogenicity and safety of live oral attenuated bovine rotavirus vaccine strain RIT 4237 in adults and young children," *Lancet* 2:807-811 (1983).

Vesikari et al., "Dose-response study of RIT 4237 oral rotavirus vaccine in breast-fed and formula-fed infants," *Pediatr. Infect. Dis. J.* 4:622-625 (1985).

Vesikari et al., "Neonatal rotavirus vaccination with RIT 4237 bovine rotavirus vaccine: a preliminary report," *Pediatr. Infect. Dis. J.* 6:164-169 (1987).

Vesikari et al., "Efficacy of two doses of RIT 4237 bovine rotavirus vaccine for prevention of rotavirus diarrhoea," *Acta. Paediatr. Scand.* 80:173-180 (1991).

Vesikari, "Clinical trials of live oral rotavirus vaccines: the Finnish experience," *Vaccine* 11:255-261 (1993).

Vesikari, "Bovine rotavirus-based rotavirus vaccines in humans," in Viral Infections of the Gastrointestinal Tract, Kapikian, ed., Marcel Dekker, Inc., pp. 419-442 (1994).

Wyatt et al., "Development of rotavirus vaccines," PAHO Copublication series No. 1, pp. 17-28 (1985).

Wyeth-Ayerst: RotaShield package insert, "Lyophilized preparation for reconstitution and oral administration," pp. 1-19 (1998).

\* cited by examiner

COMPOSITIONS AND METHOD FOR PREVENTING REACTOGENICITY ASSOCIATED WITH ADMINISTRATION OF IMMUNOGENIC LIVE ROTAVIRUS COMPOSITIONS

BACKGROUND OF THE INVENTION

Rotaviruses are a major cause of acute dehydrating diarrhea in infants and young children. Rotavirus disease accounts for 25% to 30% of gastroenteritis deaths in infants and young children in developing countries and approximately 50,000-100,000 hospitalizations of children younger than five years of age in the United States. In developing countries, it has been estimated that over 870,000 infants and young children less than 5 years of age die from rotavirus disease annually. For this reason, a safe effective vaccine is needed to prevent severe rotavirus disease in infants and young children.

A primary strategy for rotavirus vaccine development has been based on a "Jennerian" approach, which takes advantage of the antigenic relatedness of human and animal rotaviruses and the diminished virulence of animal rotavirus strains in humans. Kapikian et al., in Vaccines, Chanock et al., eds., Cold Spring Harbor Laboratory Press, Cold Spring Harbor, N.Y., pp. 151-159 (1987). Several candidate live oral rotavirus vaccines have been developed using this approach, where an antigenically-related live virus derived from a nonhuman host is used as a vaccine for immunization against its antigenically related human virus counterpart. Examples of animal rotaviruses that have been used to vaccinate humans include bovine rotavirus strain NCDV (RIT4237, Vesikari et al., *Lancet*, 2:870-811 (1983)), bovine rotavirus strain UK (Wyatt et al. PAHO Copublication series no. 1, pp 17-28 (1985), bovine rotavirus strain WC3 (Clark et al., *Am. J. Dis. Child.*, 140:350-356 (1986)) and rhesus monkey rotavirus (RRV) strain MMU 18006 (U.S. Pat. No. 4,571,385, Kapikian et al., in Vaccine 85, Lerner et al., eds., Cold Spring Harbor Laboratory Press, Cold Spring Harbor, N.Y., pp. 357-367 (1985)).

The protective efficacy among different monovalent bovine and monovalent simian rotavirus vaccines has proved to be variable (Vesikari, in Viral Infections of the Gastrointestinal Tract, Kapikian, ed., Marcel Dekker, Inc., pp. 419-442 (1994)); Kapikian ibid. pp. 443-470 (1994). Also, high concentrations of bovine rotavirus have been required to produce a satisfactory immune response in humans ($10^7$-$10^8$ plaque forming units (pfu)) (Vesikari et al., *Ped. Inf. Dis.* 4:622-625 (1985); Bernstein et al., *J. Infect. Dis.* 162:1055-1062 (1990)). The variable efficacy of these compositions can in part be attributed to the fact that the target population of two- to five-month old infants characteristically developed a homotypic immune response following vaccination (Kapikian et al., *Adv. Exp. Med. Biol*, 327:59-69 (1992); Bernstein et al., *J. Infect. Dis.*, 162:1055-1062 (1990); Green et al., *J. Infect. Dis.*, 161:667-679 (1990); and Vesikari, *Vaccine*, 11:255-261 (1993)).

Clinically relevant human rotaviruses are members of the Group A rotaviruses. These viruses share a common group antigen mediated by VP6, a protein located on the virus intermediate shell. Also, serotype specificity depends on the presence of the VP4 (protease sensitive or P type) and VP7 (glycoprotein or G type) proteins located on the virus outer shell (also often referred to as the virus capsid), both of which independently induce neutralizing antibodies (Kapikian et al., in Virology, Fields et al., eds., Raven Press, New York, N.Y., pps. 1353-1404 (1995)).

Group A rotaviruses that infect humans have been classified into ten distinct VP7 serotypes by neutralization assays. Amino acid sequence analysis has indicated that within each serotype amino acid identity within two major variable regions was high (85-100%); however, amino acid identity between strains of different serotypes was significantly less (Green et al., *Virology* 168:429-433 (1989); Green et al., *Virology* 161:153-159 (1987); and Green et al., *J. Virol.* 62:1819-1823 (1988)). Concordance between relationships among rotaviruses as determined by virus neutralization assay or sequence analysis of VP7 has been demonstrated. Therefore, a reference strain can be routinely used in clinical studies as a representative of rotavirus strains within its serotype.

To achieve protection against each of the four epidemiologically and clinically most important G serotypes (VP7) (numbered 1, 2, 3, and 4), the Jennerian approach has been modified by the production of reassortant rotaviruses. Reassortant rotavirus strains were constructed by coinfecting tissue culture cells with a rotavirus of animal origin (i.e., rhesus or bovine rotavirus) and a human rotavirus strain. Reassortant viruses produced during coinfection that contained a single human rotavirus gene encoding VP7 from the human strain and the 10 remaining rotavirus genes from the animal strain were selected by exposing the progeny of the coinfection to a set of monoclonal antibodies directed to the VP7 of the animal strain. (See, for example, U.S. Pat. No. 4,571,385; Midthun et al., *J. Clin. Microbiol.* 24:822-826 (1986); and Midthun et al., *J. Virol.* 53:949-954 (1985), incorporated herein by reference).

Studies of human×rhesus rotavirus reassortants and human×bovine rotavirus reassortants containing the VP7 gene from a human strain have demonstrated that the VP4 neutralization protein of the animal rotavirus parent dominates the immune response in infants vaccinated with these human×animal rotavirus reassortants. This probably reflects the absence of animal rotavirus VP4 antibodies among the antibodies transferred transplacentally from the mother to the infant in utero. Nevertheless, the immune response to human rotavirus VP7 that is partially blunted by maternally derived VP7 antibodies is sufficient to provide protection and thus VP7 antibodies form the basis of the modified Jennerian approach (Flores et al., *J. Clin. Microbiol.* 27:512-518 (1989); Perez-Schael et al., *J. Clin. Microbiol.* 28:553-558 (1990); Flores et al., *J. Clin. Microbiol.* 31:2439-2445 (1993); Christy et al., *J. Infect. Dis.* 168:1598-1599 (1993); Clark et al., *Vaccine* 8:327-332 (1990); Treanor et al., *Pediatr. Infect. Dis. J.* 14:301-307 (1995); Madore et al., *J. Infect. Dis.* 166: 235-243 (1992); and Clark et al., *J. Infect. Dis.* 161:1099-1104 (1990).

In studies using a single rhesus rotavirus reassortant bearing a single human rotavirus gene, namely the gene that encodes VP7, it was observed that the protective immunological response of such a reassortant was characteristically homotypic in infants less than six months of age (Green et al., *J. Infect. Dis.* 161:667-679 (1990)). This observation provided further evidence for the importance of VP7-associated immunity in immunization against rotavirus disease.

Multivalent rotavirus vaccine compositions have been developed. In particular, three human×rhesus rotavirus reassortants representing human serotypes 1, 2 and 4 have been combined with a rhesus rotavirus strain (RRV) (the latter sharing neutralization specificity with human serotype 3) to form a quadrivalent vaccine composition (RRV-TV)(Perez-Schael et al., *J. Clin. Microbiol.* 28:553-558 (1990), Flores et al., *J. Clin. Microbiol.* 31:2439-2445 (1993), each incorporated herein by reference). As with the monovalent rhesus rotavirus, the human×rhesus reassortant rotavirus vaccine compositions were found to characteristically produce a transient low level febrile condition in approximately 15% to 33% of the infants vaccinated (Perez-Schael et al., supra; Bernstein et al., *JAMA* 273:1191-1196 (1995); Flores et al., *Lancet* 336:330-334 (1995); Flores et al., *J. Clin. Microbiol.* 31:2439-2445 (1993); Halsey et al., *J. Infect Dis.* 158:1261-1267 (1988); Taniguichi et al., *J. Clin. Microbiol.* 29:483-487 (1991); Simasathien et al., *Pediatr. Infect. Dis. J.* 13:590-596 (1994); Madore et al., *J. Infect. Dis.* 166:235-243 (1992); and Joensuu et al., *Lancet* 350:1205-1209 (1997). This transient febrile episode or condition, although generally considered acceptable by the parents and health care providers of the clinical trial, could possibly be a deterrent in certain situations, such as, in premature infants who may have low levels of passively acquired maternal antibodies to rotavirus and the like.

Results of studies in humans with bovine rotavirus strains NCDV, WC3 and UK (VP7 serotype 6) indicate that these particular bovine rotavirus strains cause significantly fewer febrile reactions than the rhesus rotavirus-based vaccines. Further, bovine rotavirus was not found to be as immunogenic as the rhesus rotavirus when administered to humans. The bovine rotavirus strain NCDV (RIT4237 vaccine) has also been evaluated in neonates (Vesikari et al. *Pediatr. Infect. Dis. J.* 6:164-169 (1987)). In these trials, the bovine RIT4237 vaccine or placebo was administered to 244 newborn infants orally at a dose of $10^{8.3}$ tissue culture infectious doses 50 ($TCID_{50}$). This high dosage of the vaccine composition required to achieve infection indicated that this virus was over attenuated. The initial vaccination was not followed by a second dose. Another study was conducted with the same overattenuated vaccine composition, RIT 4237, wherein the composition was given to newborns and at 7 months of age. No vaccine associated reactions were observed (Vesikari et al., *Acta Paediatr. Scand.* 80:173-180 (1991)).

Similar studies have been conducted in newborns with a rhesus rotavirus composition (MMU-18006) as a single dose administration. No reactions could be attributed to administration of this vaccine composition. Serologic responses to the composition were not observed by complement fixation, neutralization or a rhesus rotavirus epitope-specific competition assay. The safety and immunogenicity of an oral tetravalent human×rhesus reassortant rotavirus vaccine (RRV-TV) was tested in newborns with the addition of a second dose at the age of 6 to 8 weeks to determine if immunogenicity could be enhanced (Dagan et al., *Pediatr. Infect. Dis. J.* 11:991-996 (1992)). In this study however, a positive control group of older infants, 2 to 6 months, who would be expected to develop a febrile response to vaccine with a frequency of about 15 to 30%, was not studied simultaneously. For this reason, the ability of neonatal vaccination to prevent or ablate reactogenicity associated with administration of the second dose of vaccine at 2 months of age, or later, could not be established.

The RRV-TV vaccine was licensed by the Federal Drug Administration on Aug. 31, 1998, for oral administration to infants at two (2), four (4), and six (6) months of age. It is estimated that one million doses have been administered since licensure. Post licensure surveillance detected an apparent excess in the reported incidence of intussusception in infants predominantly at vaccination. It is considered that this clustering of cases is associated with the administration of the new rotavirus composition. Although the cause of intussusception is not known several possible mechanisms for how it may occur following administration of the vaccine have been suggested, including enlargement of lymphoid tissue (Peyer's patches) along the gastrointestinal tract that might lead them to invaginate and serve as a lead point for intussusception.

With the previously licensed rotavirus composition removed from the market and the important level of protection in humans against rotavirus infection provided by vaccination, a composition or medicament for treatment or prevention of rotaviruses infection which protects against or ablates the relatively high reactogenicity of live rotavirus vaccine compositions, including the human×rhesus multivalent composition, as manifested by a transient low level febrile condition that may also reduce or eliminate intussusception in infants after immunization. Surprisingly, the present invention fulfills these and other related needs.

SUMMARY OF THE INVENTION

The present invention provides for the use of an immunogenic live rotavirus composition for the manufacture of a medicament for the treatment or prevention of a rotavirus infection without causing transient low level fever or causing intussusception, said treatment or prevention comprising administering a safe and effective amount of the immunogenic live rotavirus composition to an infant within about seven to about ten days of life followed by at least one additional administration of a safe and effective amount of the immunogenic live rotavirus composition prior to six months of age.

Compositions useful in manufacturing medicaments of the present invention can comprise a rhesus rotavirus immunologically cross-reactive with human rotavirus serotype 3. Additionally, human×rhesus rotavirus can be useful in preparation of the live immunogenic composition. Typically, the composition comprises a plurality of human×rhesus reassortant rotaviruses of different serotypes which are clinically relevant. Such a multivalent human×rhesus rotavirus composition can also be manufactured to contain a rhesus rotavirus immunologically cross-reactive with human rotavirus serotype 3. One particularly useful composition comprises a human×rhesus reassortant rotavirus of human rotavirus serotype 1, a human×rhesus reassortant rotavirus of human rotavirus serotype 2, a human×rhesus reassortant rotavirus of human rotavirus serotype 4, and a rhesus rotavirus immunologically non-reactive with human rotavirus serotype 3.

In another embodiment of the present invention, plurality of a human×bovine reassortant rotavirus can be useful in the manufacture of the immunogenic live rotavirus composition for the treatment and prevention of rotarvirus infection without causing transient low level level or causing intussusception. The compositions can comprise a plurality of human×bovine reassortant rotaviruses of different serotypes which are clinically relevant. Particularly useful are compositions which comprise a human×bovine reassortant of human rotavirus serotype 1, a human×bovine reassortant of human rotavirus serotype 2, a human×bovine reassortant of human rotavirus serotype 3, and a human×bovine reassortant rotavirus of human rotavirus serotype 4. The compositions can further comprise human×bovine reassortant rotavirus including, for example, those of human rotavirus serotypes 5 and/or 9, or a bovine×bovine reassortant rotavirus with human rotavirus VP7 serotype 10 specificity, or a human rotavirus serotype VP4 1AX bovine rotavirus UK reassortant.

Immunogenic compositions can be formulated as a medicament wherein each rotavirus or reassortant rotavirus is administered separately or in various compositions. Typically, the medicament is formulated as a combined composition comprising a plurality or rotavirus and/or reassortant rotavirus of a human rotavirus serotype. The medicament comprising the immunogenic live rotavirus can be formulated for administration to the alimentary tract of an individual. Typically, a liquid suspension is used for administration of the medicament of the present invention.

For the treatment or prevention of rotavirus without causing transient low level fever and without causing intussusception, the medicament comprising a safe and effective amount of the immunogenic live rotavirus compositions is administered within about seven to about ten days of life followed by at least one additional administration of a safe and effective amount of the medicament comprising an immunogenic live rotavirus composition prior to six months of age. Typically, the second administration of the medicament of the present invention is at about 6 to about 10 weeks of age or at about 14 to about 18 weeks of age. A subsequent administration of the medicament is at about 14 to 18 weeks of age or about 22 to about 26 weeks of age respectively.

DESCRIPTION OF THE SPECIFIC EMBODIMENTS

The present invention provides compositions and methods useful for preventing reactogenicity associated with the administration of immunogenic live rotavirus compositions in humans. The compositions useful in the manufacture of a medicament for the prevention and treatment of rotavirus infection without causing transient low level fever typically seen when infants received their first dose of the rotavirus composition between about 2 to 6 months of age and further, to reduce the risk of intussusception in infants 3 to 7 days following the first dose of the rotavirus composition.

As used herein, "reactogenic" or reactogenicity denotes a mild transient fever occurring during the week following administration of the immunogenic composition. A fever is defined in the context of the present invention as the development of a rectal temperature of greater than or equal to 38.1° C. in a pediatric vaccinee.

The compositions of the present invention elicit the production of an immune response that is at least partially protective against symptoms of serious rotaviral disease, such as severe diarrhea and dehydration, when the individual is subsequently infected with a wild-type human rotavirus strain. As the reasserted viruses of the immunogenic composition infect the host alimentary tract, typically the immunogenic composition of the present invention will not cause clinically relevant fever or reaction in the vaccinee. Following vaccination, there are detectable levels of host engendered serum antibodies which are capable of neutralizing the serotypes of rotavirus that make up the immunogenic composition. In particular, the multivalent immunogenic composition of the present invention will produce an immunological response to most, if not all, of the clinically relevant group A human rotaviruses prevalent in different settings. The teachings of the present invention are not limited to those human rotavirus serotypes currently recognized of clinically relevant, but also include those serotypes of human rotavirus that may emerge as clinically relevant in the future.

The reassorted rotavirus which is a component of the multivalent immunogenic composition used in the methods of the present invention is administered in an isolated and typically purified form. By isolated is meant to refer to reassorted rotavirus that has been separated from other cellular and viral products of its manufacture, such as wild type virus and other heterologous components of a cell culture or other systems.

Generally, rotavirus reassortants are produced by coinfection of mammalian cells in culture with a tissue culture-adapted animal rotavirus, i.e., bovine, rhesus, and the like, and a tissue culture-adapted human rotavirus. Typically, African green monkey kidney (AGMK) cells are used as the host cells for co-infection. Following co-infection with the animal and human rotavirus strains, selection of the desired reassortant is typically achieved by exposing the growth yield of co-infected cultures to neutralizing antibodies specific for the protein product of the animal rotavirus gene that is to be replaced by the human rotavirus gene (See, U.S. Pat. No. 4,571,385, incorporated herein by reference). In particular, polyclonal serum or monoclonal antibody specific for rhesus or bovine rotavirus VP7 and/or VP4 proteins can be used. After several rounds of plaque purification and subculture, selected reassortants are characterized for serotype and genotype. Serotype is typically determined by plaque reduction neutralization (PRN) assay or enzyme immunoassay. Genotype is typically determined by gel electrophoresis and RNA-RNA hybridization of the viral genome. Rotavirus reassortants having only the human VP7 or VP4 gene are typically selected in the present multivalent immunogenic compositions. Reassortants comprising multiple human rotavirus genes can also be used. In this regard, reassortant rotaviruses of interest are particularly those encoding the human rotavirus VP7 and/or the human rotavirus VP4 gene products.

In the present invention, particularly preferred rotavirus reassortants are human rotavirus and rhesus rotavirus reassortants comprising the human rotavirus gene encoding VP7 and the remaining ten rotavirus genes of rhesus rotavirus origin. Other animal rotavirus strains can also be used to make reassortant rotavirus as long as the compositions are capable such as bovine UK rotavirus of inducing a serologic response in a vaccinee when administered at a dosage of about $10^{6.0}$ plaque forming units for each rotavirus serotype.

Propagation of the reassorted rotavirus can be in a number of cell cultures which support rotavirus growth. Preferred cell cultures for propagation of rotavirus reassortants for vaccine use include primary or secondary simian African green monkey kidney cells (AGMK), qualified diploid simian FRhL-2 cells and qualified simian heteroploid Vero cells. Cells are typically inoculated with rotavirus reassortants at a multiplicity of infection ranging from about 0.1 to 1.0 per cell, or more, and are cultivated under conditions appropriate for viral replication, for about 3-5 days, or as long as necessary for virus to reach an adequate titer. Rotavirus reassortants are harvested from infected cell culture and separated from cellular components, typically by well known clarification procedures, e.g., centrifugation, and may be purified as desired using procedures well known to those skilled in the art.

In a preferred embodiment for use as an immunogenic composition, a human×rhesus reassortant rotavirus of VP7 serotype 1, serotype 2, and serotype 4, and a rhesus rotavirus cross-reactive with human rotavirus serotype 3 are used as a quadrivalent vaccine. Typically, the immunogenic composition will be admixed to form a combined composition for simultaneous administration. The final ratio of each rotavirus serotype is determined by the immunogenicity of the individual rotavirus reassortants. Although not preferred, each rotavirus or reassortant rotavirus, can also be administered in a sequential manner to provide an effective vaccine formulation.

The immunogenic composition may be introduced into a host, particularly humans, with a physiologically acceptable carrier and/or adjuvant. Useful carriers include, e.g., citrate-bicarbonate buffer, buffered water, normal saline, and the like. The resulting aqueous solutions may be packaged for use as is, or lyophilized, as desired, using lyophilization protocols well known to the artisan. Lyophilized virus will typically be maintained at about 4° C. When ready for use the lyophilized preparation is combined with a sterile solution prior to administration, as mentioned above.

The compositions may contain pharmaceutically acceptable auxiliary substances as required to approximate physiological conditions, such as pH adjusting and buffering agents and the like, for example, sodium acetate, sodium lactate, sodium chloride, potassium chloride, calcium chloride, sorbitan monolaurate, tri-ethanolamine oleate, citrate-bicarbonate, or the like. When the composition is administered orally it may also be necessary to provide the individual a buffer solution to partially neutralize stomach acid and protect the reassortant rotavirus while passing to the intestine. Buffer solutions appropriate for this use include sodium bicarbonate, citrate bicarbonate, or the like. Upon immunization with a human×bovine reassortant rotavirus composition of the present invention, particularly via the oral route, the immune system of the host responds to the composition by producing both local secretory and serum antibodies specific for the rotavirus proteins. As a result of the administration of the composition, the host becomes at least partially or completely immune to human rotavirus disease caused by a wild-type strain that corresponds to the immunizing serotype(s). If wild-type virus infection does occur, the host is resistant to developing moderate or severe rotaviral disease, particularly of the gastrointestinal tract.

The multivalent immunogenic compositions of the present invention containing the human×rhesus reassortant rotaviruses and rhesus rotavirus are administered to an infant, particularly a neonate, susceptible to or otherwise at risk of rotavirus disease to induce the individual's own immune response capabilities. Such an amount is defined to be an "immunogenically effective dose." Immunogenicity or "immunogenically effective dose" as used in the present invention means the development in a vaccinee of a cellular and/or antibody mediated immune response to the vaccine composition. Usually such a response consists of the vaccinee producing serum antibodies, B cells, helper T cells, suppressor T cells, and/or cytotoxic T cells directed specifically to an antigen or antigens included in the vaccine composition of the present invention. A four-fold or greater rise above a preinoculation antibody titer following immunization measured by a rotavirus group specific, or rotavirus serotype-specific assay is considered a significant response.

In this method, the precise amount of each human×rhesus reassortant rotaviral serotype and rhesus rots virus in a particular immunogenic composition depends on the patient's age, state of health and weight, the mode of administration, the nature of the formulation, etc., but generally the range was from about $10^4$ to about $10^6$ plaque forming units, preferably from about $10^5$ to less than $10^6$ plaque forming units (pfu) of each serotype per patient.

In any event, the immunogenic composition should provide a quantity of each reassortant rotavirus sufficient to induce an individual's immune response against rotavirus disease. Preferably, this immune response will effectively protect the individual against serious or life-threatening rotavirus disease. In some instances it may be advantageous to combine the rotaviral compositions used in the methods of the present invention with other serotypes of human rotavirus or other infectious agents, particularly other gastrointestinal viruses. For example, the rotaviral compositions used herein can further include, for example, human×rhesus reassortant rotavirus of serotype 5 (Timenetsky et al., *J. General Virol.* 78:1373-1378 (1997)), and/or serotype 9 (Nakagomi et al., Microbiol. Immunol. 34:77-82 (1990)), and/or serotype 10, and/or human×rhesus reassortant rotavirus of VP4 serotype 1A. Administration can be simultaneous (but typically separately) or sequentially with another possible gastrointestinal virus vaccine, such as a human calicivirus (e.g., Norwalk virus) or related vaccine.

In other embodiments, the invention provides for administration to a neonate an immunogenically sufficient amount of a multivalent human×bovine reassortant rotavirus composition comprising at least four VP7 serotypes of human rotavirus. In one embodiment the human×bovine reassortant rotavirus which comprise the composition include a human rotavirus serotype 1×bovine rotavirus strain UK, a human rotavirus serotype 2×bovine rotavirus strain UK, a human rotavirus serotype 3×bovine rotavirus strain UK, and a human rotavirus serotype 4×bovine rotavirus strain UK. The multivalent composition can also include, but is not limited to, i.e., a human×bovine reassortant rotavirus of serotype 5, and/or serotype 9, or a bovine×bovine reassortant rotavirus with human rotavirus VP7 serotype 10 specificity, or a human rotavirus serotype VP4 1A×bovine rotavirus UK reassortant and the like. Further, as additional rotavirus serotypes are recognized as important in human disease, they too can be added to an immunogenic composition of the present invention and used in methods for stimulating the immune system to produce an immunogenic response to currently recognized and newly recognized rotaviruses of clinical significance.

Single or multiple administrations of the immunogenic compositions of the invention can be carried out. In neonates and infants, multiple administrations may be required to elicit a sufficient level of immunity, particularly where there are high levels of maternally derived antibodies specific for rotavirus. Administration should begin within the first 7 to 10 days of life, and continue at intervals such as one to two months or more after the initial immunization, or as necessary to induce and maintain sufficient levels of immunity against human rotavirus infection. Levels of induced immunity can be monitored by measuring amounts of rotavirus group-specific antibodies or serotype-specific neutralizing antibodies in serum and secretions, and dosages adjusted or vaccinations repeated with one or more serotypes of a multivalent reassortant rotavirus composition of the present invention when necessary to maintain desired levels of immunity.

Thus, the methods of the invention specifically comprise a the administration of an immunogenically sufficient amount of an immunogenic rotavirus composition to a neonate in need of immunological protection against rotavirus followed by a second dose at about 2 to 4 months, and optionally a third dose at 4 to six, or even 8 to 12 months of age. Administration of the first dose prior to the tenth day of life has been demonstrated to prevent the transient febrile condition observed when the composition is initially administered at 2 to 6 months of age.

The following examples are offered by way of illustration, not by way of limitation.

EXAMPLE

This example describes the administration of live oral rhesus tetravalent (RRV-TV) vaccine in a double-blind placebo-controlled trial to compare the reactogenicity and immunogenicity of the composition when given at approximately 0, 2, and 4 months; 0, 4 and 6 months; or 2, 4, and 6 months. Placebo was administered at approximately 6 months to the first group, at 2 months for the second group and at 0 months for the third group.

Most of the clinical procedures for the pediatric studies were also identical to those described by Halsey et al., *J. Infect. Dis.* 158:1261-1267 (1988)(incorporated herein by reference), with a few exceptions. Briefly, routine childhood immunizations appropriate for the child's age were given on schedule. Each pediatric subject was randomized to receive rotavirus or placebo. Buffered diluent (sodium-bicarbonate; citric acid) was used for reconstituting the lyophilized vaccine after which 2.5 ml of the mixture was withdrawn into the dispette and administered orally. There were no feeding restrictions before or after vaccination.

Rectal temperatures were taken daily and symptoms, if any, were recorded for 7 days. Study subjects were considered to have "rotavirus-like illness," (i.e., an illness that could possibly be caused by a rotavirus, if they had diarrhea, or any episode of frank vomiting or fever during the 7-day period after oral administration of rotavirus. Diarrhea was defined as three or more unformed stools within 48 hours. Fever was defined as a rectal temperature >38° C.

Blood was collected from each study participant before vaccination (cord blood); approximately one month after the second and third dose of "vaccine" (i.e., at approximately 5 and 7 months of age); and 4-6 weeks after administration of rotavirus for measurement of rotavirus-specific antibodies. Prevaccination and postvaccination sera were tested for rotavirus-specific IgA and IgG antibodies by ELISA, using rhesus rotavirus as a group-specific antigen as described in Midthun et al., *J. Clin. Microbiol.* 27:2799-2804 (1989) and Hoshino et al., *J. Clin. Microbiol.* 21:425-430 (1985); each incorporated by reference herein. The 3 sera were also tested by plaque reduction neutralization (PRN) antibody assay as described in Midthun et al., *J. Clin. Microbiol.* 27:2799-2804 (1989). A fourfold or greater rise in antibody titer in the postvaccination serum compared to the prevaccination serum measured by ELISA IgA or PRN antibody assay was considered a significant response.

The rates of illness of vaccinees and placebo recipients and the rates of serologic response for these groups within each age group and in each study are compared using a two-tailed Fisher's exact test.

None of the 62 infants, who received RRV-TV vaccine at neonatal age, had fever. Of the neonatally vaccinated infants, 0 of 32 who received a second dose at 2 months of age, had fever as compared with this indicates that neonatal immunization provided a level of protection sufficient to prevent adverse reaction to the second dose of vaccine administered at the time (i.e., 2 months of age) at which vaccine reactogenicity is characteristically expressed. This level of resistance to rotavirus should serve as a foundation for a significant booster response to the second and third doses of vaccine. Seroconversion by rhesus rotavirus neutralizing antibodies occurred in 71%, 86% and 89% and rotavirus IgA antibodies were detected in 68%, 87%, and 96% of the infants after immunization schedules 0-2-4; 0-4-6 and 2-4-6 months, respectively.

Despite what appears to be lower immunogenicity, administration of RRV-TV vaccine in the neonatal period is an alternative to the previously recommended 2-4-6 month schedule because of lower reactogenicity and thus apparently greater safety. In addition, by administering the first dose in the neonatal age, advantage is taken of the relatively refractory period during the first two months of life for the development of intussusception (Rennels et al., *Ped Infant* 10:924-925 (1998); Gay et al., *Lancet* 354:956 (1999)). Also, the absence of fever after the second dose of vaccine at 2 months of age may be a signal of restricted multiplication of the vaccine during this critical period when the incidence of intussusception begins its ascent (Rennels et al., ibid.; Fay et al., ibid). Neonatal immunization with the use of bovine rotavirus based vaccine, already known to be more attenuated than rhesus rotavirus but just as immunogenic, should provide a considerable increase in safety reassured by not only a lack of reactogenicity but also significant reduction in vaccine induced intussusception.

Although the foregoing invention has been described in some detail by way of illustration and example for purposes of clarity of understanding, it will be obvious that certain changes and modifications may be practiced within the scope of the appended claims. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted.

What is claimed is:

1. A method for reducing the incidence of a transient low level fever and/or intussusception associated with administration of a live rhesus rotavirus immunogenic composition to an infant which comprises administering the live rhesus rotavirus immunogenic composition to the infant within about the first 7 to about 10 days of life followed by at least one booster immunization prior to 6 months of age.

2. The method according to claim 1, wherein the composition comprises a rhesus rotavirus immunologically cross reactive with human rotavirus serotype 3.

3. The method according to claim 1, wherein the composition comprises a human x rhesus reassortant rotavirus.

4. The method according to claim 3, wherein the composition comprises multiple human x rhesus reassortant rotaviruses of different serotypes.

5. The method according to claim 4, wherein the composition comprises multiple human x rhesus reassortant rotaviruses of different serotypes and a rhesus rotavirus immunologically cross reactive with human rotavirus serotype 3.

6. The method according to claim 5, wherein the composition comprises a human x rhesus reassortant rotavirus of human rotavirus serotype 1, human rotavirus serotype 2 and human rotavirus serotype 4 and a rhesus rotavirus immunologically cross reactive with human rotavirus serotype 3.

7. The method according to claim 4, wherein each rotavirus of a human rotavirus serotype is administered separately.

8. The method according to claim 4, wherein each rotavirus of a human rotavirus serotype is administered in a combined composition.

9. The method according to claim 1, wherein the composition is administered to the alimentary tract of an individual.

10. The method according to claim 9, wherein the composition is administered as a liquid suspension.

11. The method according to claim 6, wherein the booster is administered at about 6 to about 10 weeks of age.

12. The method according to claim 11, wherein a further booster is administered at about 14 to about 18 weeks of age.

13. The method according to claim 6, wherein the booster is administered at about 14 to about 18 weeks of age.

14. The method according to claim 13, wherein a further booster is administered at about 22 to about 26 weeks of age.

* * * * *